(12) United States Patent
Loos

(10) Patent No.: US 8,999,727 B2
(45) Date of Patent: Apr. 7, 2015

(54) INNOVATIVE TSH-R-AB-KIT

(75) Inventor: Ulrich Loos, Baden-Württemberg (DE)

(73) Assignee: Ulrich Loos, Baden-Wurttemberg (DE)

( * ) Notice: Subject to any disclaimer, the term of this patent is extended or adjusted under 35 U.S.C. 154(b) by 1678 days.

(21) Appl. No.: 11/992,563

(22) PCT Filed: Sep. 25, 2006

(86) PCT No.: PCT/EP2006/066719
§ 371 (c)(1),
(2), (4) Date: May 1, 2009

(87) PCT Pub. No.: WO2007/036511
PCT Pub. Date: Apr. 5, 2007

(65) Prior Publication Data
US 2009/0325310 A1    Dec. 31, 2009

(30) Foreign Application Priority Data

Sep. 26, 2005   (DE) .......................... 10 2005 046 022

(51) Int. Cl.
*G01N 33/76* (2006.01)
*G01N 33/53* (2006.01)
*C07K 14/72* (2006.01)
*G01N 33/564* (2006.01)

(52) U.S. Cl.
CPC ............... *G01N 33/76* (2013.01); *G01N 33/53* (2013.01); *C07K 14/723* (2013.01); *G01N 33/564* (2013.01)

(58) Field of Classification Search
None
See application file for complete search history.

(56) References Cited

U.S. PATENT DOCUMENTS 7,229,762 B2 * 6/2007 Stamler et al. ............... 435/6.14
7,955,602 B2 * 6/2011 Hanash et al. ............. 424/184.1

FOREIGN PATENT DOCUMENTS

| EP | 1 078 986 | 8/2000 |
| WO | WO 99/64865 | 12/1999 |
| WO | WO 00/00590 | 1/2000 |
| WO | WO 01/63296 | * 8/2001 |

OTHER PUBLICATIONS

Minich, W.B., and Loos, U. Exp. Clin. Endocrinol. Diabetes. 2000;108:110-119.*
Kemp, Bruce E., "Autologous Red Cell Agglutination Assay for HIV-1 Antibodies: Simplified test with Whole Blood", Science, vol. 241 (1988), pp. 1352-1354.
Minich, W., "Expression of a Functional Tagged Human Thyrotropin Recept. in HeLa Cells Using Recombinant Vaccinia Virus", Exp.& Clin. Endo. & Diabetes, 105(1997)pp. 282-290.
Minich, W., "Isola. of Radiochem. Pure I-Labeled Human Thyrotro. Recept.& its Use for Detect. of Pathol. Autoantibodies in Sera fr. Graves' Patients",J.of Endo.160(1999)239-45.
Nakabayashi, K."Thyrostimulin, a Heterodimer of Two New Hum. Glycoprotein Hormone Subunits, Activ. Thyroid-Stimul. Hormone Recept.", J. of Clin.Invest. 109, 11(2002)pp. 1445-1452.
Tahara, K, "Epitopes for Thyroid Stimulating & Blocking Autoantibodies on the Extracellular Domain of the Human Thyrotropin Receptor", Thyroid, vol. 7, No. 6,(1997)pp. 867-877.
Tahara, K, "Immunoglobulins from Graves' Disease Patients Interact w/Diff. Sites on TSH Receptor/LH-CG Receptor Chimeras . . . " Bio. & Biophy. Res. Comm. 179, 1,(1991)70-77.
Wilson, Kim M., "Rapid Whole Blood Assay for HIV-1 Seroopositivity Using an Fab-Peptide Conjugate", Journal of Immunological Methods, 138 (1991), pp. 111-119.

* cited by examiner

*Primary Examiner* — Gerald R Ewoldt
(74) *Attorney, Agent, or Firm* — Honigman Miller Schwartz and Cohn LLP; Cynthia M. Bott; Jonathan P. O'Brien

(57) ABSTRACT

Methods are described for detection of autoimmune antibodies against the TSH receptor using TSH receptor chimeras, which preferably only contain the extracellular portion of the TSH wild type receptor modified as chimera, and are modified by highly immunogenic peptide residues or by enzymes suitable for detection, wherein the determination methods described allow simple detection of stimulating, blocking and neutral autoimmune antibodies.

17 Claims, 6 Drawing Sheets

Standard curve bridge assay: polynomial function over a wide measuring range

Standard curve with WHO standard for thyroid-stimulating antibodies 90/672

Detection of sTRAb in the bridge assay

B/B0: The RLU average of each standard divided by the RLU average of the zero standard (n = 3).

INNOVATIVE TSH-R-AB-KIT

This application is a U.S. National Phase Application of PCT Application No. PCT/EP2006/066719, which was filed on Sep. 25, 2006, and claims priority to German Patent Application DE 10 2005 046 022.4, which was filed on Sep. 26, 2005. Both of these applications are incorporated herein in their entirety.

TECHNICAL FIELD OF THE INVENTION

The invention relates to methods for detection of different types of autoimmune antibodies against the receptor for the thyroid-stimulating hormone (TSH receptor) with high specificity, and to new TSH receptor chimeras applicable in this method as binding reagent.

TECHNICAL BACKGROUND OF THE INVENTION

The TSH receptor (TSH-R) plays a key role in function and growth of thyroid cells. This receptor is a member of a subfamily of G-protein-coupled glycoprotein receptors, which additionally in particular also comprise receptors for the luteinizing hormone/chorionic gonadotropin (LH/CGR) and the follicle-stimulating hormone (FSHR). The receptors of this subfamily have a large N-terminal extracellular domain, which is of essential significance for ligand binding, and for which it was shown, that it is involved in signal transfer. The transfer of the TSHR signal is mainly mediated by activating adenylate cyclase, which results in an increase of the intracellular cAMP level.

Part of the large interest in the TSH receptor is to be attributed to its role as primary auto-antigen for thyroid gland autoimmune diseases, which are accompanied by the occurrence of auto-antibodies against the TSH receptor. Such thyroid gland autoimmune diseases in particular include Basedow's disease, an autoimmune disease resulting in hyperthyroidism, which is one of the most frequent human autoimmune diseases. Basedow's disease is caused by activation of adenylate cyclase and the resulting cAMP increase. This results in hyperthyroidism, goiter formation, and possibly eye changes. The auto-antibodies against the TSH receptor can also be of a blocking nature, and thus inhibit adenylate cyclase and cAMP. In this case, there is a hypofunction of the thyroid gland. Simultaneous occurrence of stimulating and blocking auto-antibodies in the affected patients is likewise possible, wherein the portion of stimulating antibodies usually predominates.

For detection of such autoimmune antibodies, there has been a bioassay for some time now, in which the cAMP increase is measured. This measuring method is very time-consuming. Furthermore, the bioassay is not reliable, since it can provide false-positive results. Within the scope of this description, this type of measuring method will be designated as bioassay to differentiate it from the in-vitro methods for determination of autoimmune antibodies against the TSH receptor. In an in-vitro detection method for autoimmune antibodies available on the market, a TSH receptor extracted from pork thyroid gland membrane is used (first generation of in-vitro methods). In another assay for detection of autoimmune antibodies against the TSH receptor, a complete human recombinant TSH receptor protein (wild type) is used in a competition assay (second generation of in-vitro methods).

Thyroid, Vol. 7 (1997) 867-877 describes the epitopes for stimulating and blocking antibodies at the TSH receptor. The majority of the functional epitopes for stimulating antibodies are located in the range of amino acids 8 to 168, and those for the blocking antibodies in the range of amino acids 261 to 370 of the receptor protein. For activity measurements, the above stated bioassay is used.

WO 01/27634 A1 for the first time provides a quantitative method for simultaneous detection of autoimmune antibodies of different specificity, which is quickly reproducible and executable with high accuracy. For this purpose, TSH receptor chimeras are used, which differ from the wild type receptor in that individual sequences, to which autoimmune antibodies bind, are substituted with respective sequences of another receptor from the class of G-protein-coupled receptors. The TSH receptor chimeras are based on the complete TSH receptor protein. However, the measuring effort is high. The separation by centrifugation makes the method too cumbersome for routine use. The assay also must be executed in an ice bath or at 4° C., since the TSH receptor chimeras are not very stable. A respective technical teaching can be found in WO 01/63296 A1, where the use of a sandwich technique is suggested for detection. It turned out, however, that usually with the assay materials suggested there, unspecific binding is too high. An assay for detection of autoimmune antibodies on the basis of the findings of the two patent applications stated above is not available on the market.

For the purpose of this description, a measuring method for detection of autoimmune antibodies available on the market for some time now, which uses the complete unchanged TSH receptor in a competition assay, will be designated as second-generation detection method. This assay is suitable for detection of Basedow's disease. It is, however, disadvantageous that stimulating, blocking and neutral autoimmune antibodies cannot be distinguished. Furthermore, not all subtypes are identified, since the displaced TSH only binds to the epitope for stimulating and blocking auto-antibodies at 30 to 40%.

SUMMARY OF THE INVENTION

Starting from this state of the art, the object underlying the invention is to modify the method known from WO 01/27634 A1 to further increase the accuracy and expressiveness of this assay, and to make such a method usable for automats.

This object is solved by a method for differential determination of different types of auto-antibodies directed against the TSH receptor in patient samples using TSH receptor chimeras as binding reagent, in which the sequences of the receptor substantial for binding stimulating and/or blocking auto-antibodies are replaced by respective sequences of another receptor, which do not effect any binding of the respective type of auto-antibodies, by (a) contacting the patient sample with first TSH receptor chimeras bound to a solid phase, wherein an autoimmune antibody with an antigen-binding fragment binds to the first TSH receptor chimera, (b) adding a second, C-terminal-modified receptor chimera, wherein the other antigen-binding fragment of the autoimmune antibody binds to the second C-terminal-modified TSH receptor chimera, and finally (c) admixing a labeled secondary antibody directed against the modified C-terminal epitope of the second receptor chimera, wherein this antibody binds to the modified C-terminal epitope of the second TSH receptor chimera, and triggers a detectable event, or using a second receptor chimera labeled in such manner, that this chimera can be detected by known detection methods.

According to a further embodiment, the object underlying the invention, can also be solved by (a) contacting the patient sample with binding agent adsorbed to a solid phase, the binding agent being selected from protein A, protein G, and anti-IgG, to allow binding of an autoimmune antibody from the patient sample to the binding agent,
(b) admixing a TSH receptor chimera to the mixture of binding agent adsorbed to a solid phase and patient sample, to allow binding of an autoimmune antibody to the TSH receptor chimera,
(c) admixing to the received reaction mixture a labeled modified secondary antibody (F(ab)s), to allow binding of the secondary antibody at the receptor chimera to an epitope of the receptor chimera other than the epitope, to which the autoimmune antibody binds, and wherein the secondary antibody is modified in such manner, that it does not bind to the binding agent adsorbed to a solid phase (Fab regions only), or
using at stage (b) a TSH receptor chimera labeled for executing a common detection.

Subject of the invention are furthermore TSH receptor chimeras, in which the sequences of the receptor substantial for binding of stimulating and/or blocking auto-antibodies are replaced by respective sequences of another receptor, which do not effect any binding of the respective type of auto-antibodies, and the TSH receptor chimeras are truncated and therefore neither contain the membrane portion nor the intracellular portion of the TSH receptor protein.

DESCRIPTION OF THE PREFERRED EMBODIMENTS

Figure 1:
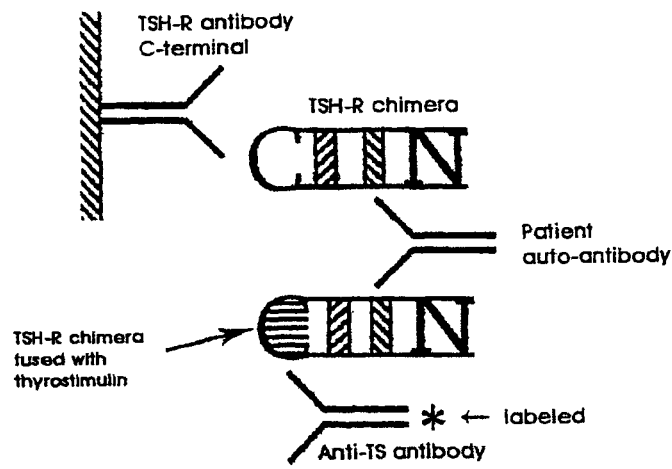
FIG. 1 shows schematically a procedure according to the invention.

Sequence No. 1 shows the nucleotide sequence of a truncated TSH receptor chimera B (extracellular-portion) fused with the secretory alkaline phosphatase.

Sequence No. 2 shows the amino acid sequence of a truncated TSH receptor chimera B (extracellular portion) fused with the secretory alkaline phosphatase.

Sequence No. 3 shows the nucleotide sequence of a fusion protein from a truncated TSH receptor chimera B (extracellular portion) fused with an immunogenic epitope.

Sequence No. 4 shows the amino acid sequence of a fusion protein from a truncated TSH receptor chimera B (extracellular portion) fused with an immunogenic epitope.

Sequence No. 5 shows the nucleotide sequence of a fusion protein from a truncated TSH receptor chimera A (extracellular portion) fused with the secretory signal peptide of the secretory alkaline phosphatase (SEAP) and the SEAP.

Sequence No. 6 shows the amino acid sequence of a fusion protein from a truncated TSH receptor chimera A (extracellular portion) fused with the secretory signal peptide of the SEAP and the SEAP.

Sequence No. 7 shows the nucleotide sequence of a fusion protein from a truncated TSH receptor chimera A (extracellular portion) fused with a highly immunogenic epitope for a polyclonal antibody.

Sequence No. 8 shows the amino acid sequence of a fusion protein from a truncated TSH receptor chimera A (extracellular portion) fused with a highly immunogenic epitope for a polyclonal antibody.

Sequence No. 9 shows the nucleotide sequence of a fusion protein from a truncated TSH receptor chimera B (extracellular portion) fused with a gLUC signal peptide sequence and a Gaussia luciferase sequence.

Sequence No. 10 shows the amino acid sequence of a fusion protein from a truncated TSH receptor chimera B (extracellular portion) fused with a gLUC signal peptide sequence and a Gaussia luciferase sequence.

The TSH receptor chimeras used according to the invention are such for which portions of the amino acid sequence are replaced by comparable sequences of another receptor with a different binding behavior towards TSH receptor autoimmune antibodies, in particular non-binding sequences. Such comparable sequences may for example be sequences of a rat LG-CG receptor. Therefore, those epitopes were substituted in the receptor chimeras used according to the invention, to which stimulating and/or blocking autoimmune antibodies bind. For the TSH receptor chimeras, to which neutral autoimmune antibodies bind, therefore the epitopes for stimulating and for blocking autoimmune antibodies were substituted. These receptor chimeras can be constructed according to Biochem. Biophys. Res. Comun. (1991), 179: 70-77 or WO 01/27634. Both documents are incorporated by reference for the purposes of disclosure of this invention.

Thus, according to the invention, the TSH receptor chimeras A, B and C can be distinguished. For chimera A, preferably the TSH receptor amino acids 8 to 165 can be replaced by substantially the comparable amino acids 10 to 166 of the LH-CGR. For chimera B, preferably the TSH receptor amino acids 261 to 370 can be replaced by substantially the respective amino acids 261 to 329 of a rat LH-CGR. For chimera C, amino acids 8 to 165 as well as amino acids 261 to 370 of the TSH receptor can be replaced by respective LH-CGR amino acids.

With TSH receptor chimera A blocking autoimmune antibodies, with chimera B stimulating autoimmune antibodies, and with chimera C neutral autoimmune antibodies are detected from a patient sample.

The TSH receptor extends from the cytosol through the cell membrane into the extracellular space. The extracellular portion of the receptor protein has the binding site for TSH and the autoimmune antibodies. Surprisingly, it was found, that a truncated TSH receptor peptide, which substantially only has the extracellular portion of the TSH receptor protein, can be stored stablely, without loosing its ability to bind TSH. The same was also found for its ability to bind autoimmune antibodies.

Preferably, the TSH receptor chimeras A, B, or C used according to the invention are only the extracellular portion of the respective TSH receptor chimera (truncated TSH receptor chimera). This applies to the so-called first TSH receptor chimera used in the method according to the invention as well as to the so-called second additionally used TSH receptor chimera. This extracellular portion of the TSH receptor chimera can substantially comprise a peptide of 1 to 418 amino acids. That corresponds to amino acids 1 to 418 of the extracellular portion of the wild type TSH receptor. The preferably used truncated TSH receptor chimeras A, B, and C are thus substantially missing the cytosolcytosolic portion and the membrane portion of the known TSH receptor chimeras. The use of the truncated TSH receptor chimeras in the detection methods according to the invention is substantially simpler than that of the complete TSH receptor chimeras known so far.

Preferably, the TSH receptor chimeras A, B, and C according to the invention are therefor such ones missing the cytosol portion and substantially the membrane portion of the TSH wild type receptor. The extracellular portion of the wild type TSH receptor is in these cases formed as chimera A, B, or C, like described above.

Particularly advantageous in these truncated TSH receptor chimeras is that for their production in recombined cells, the truncated TSH receptor chimeras A, B, and C are secreted into the extracellular space, when signal peptides or the respective nucleotide sequence, respectively, of, for example, the alkaline phosphatase or the transthyretin are inserted upstream of the TSH receptor chimera nucleotide sequence. Then no digestion of the cells is required to obtain the TSH receptor chimeras A, B, or C. Particularly preferred is the signal peptide of the enzyme transthyretin. In this description of the invention, signal peptide means a peptide residue, which has at least the amino acids required for the secretion of the truncated receptor chimeras from the cell.

According to a further preferred embodiment, the signal peptide is a constituent of the TSH receptor chimeras, and additionally an enzyme with its secretory signal peptide sequence effective for detection purposes can be contained in the TSH receptor chimera.

In one embodiment of the invention, the first TSH receptor chimera bound to a solid phase can be fused at its C-terminal end with a peptide. Such a peptide is, for example, a highly immunogenic subsequence of the peptide thyrostimulin or from the C-terminal end of the TSH receptor. In this case, the antibody immobilizing the first TSH receptor chimera at the solid phase is a monoclonal or polyclonal antibody directed against this peptide, for example an antibody directed against thyrostimulin.

In a further embodiment of the invention, a so-called second TSH receptor chimera can be modified at its C-terminal end in such manner, that specific binding of the second TSH receptor chimera to the immobilized antibody, to which a first TSH receptor is bound already with its C-terminal end, is avoided. Thus problems like unspecific binding, which can occur in a bridge assay, are suppressed. The use of this second receptor chimera modified in such manner serves the further increase in specificity and sensitivity of the method.

According to a further embodiment, the modified second TSH receptor chimera described above can be fused at its C-terminal end with a highly immunogenic peptide. Such a peptide can be selected from a subsequence of thyrostimulin or the C-terminal end of the TSH receptor. Such a subsequence can be obtained from the cytosolic portion of the TSH receptor, for example encoded by nucleotides 743 to 763 of the TSH receptor. A second TSH receptor chimera obtained in such manner also has the advantage, that binding of the second TSH receptor chimera to the immobilized antibody, to which a first TSH receptor chimera is bound already with its C-terminal end, is avoided. With the presentation of a highly immunogenic peptide residue, a second labeled antibody can be bound simply and specifically. The fusion of a subsequence of the peptide thyrostimulin results in the same advantage. Antibodies against highly immunogenic peptide sequences show high binding affinity. Consequentially, high binding specificity is achieved, whereas unspecific binding is largely reduced.

The first or second TSH receptor chimera used according to the invention can be modified for detection. This modification can be labeling for detection or labeling by an immunogenic peptide sequence, which is detected by a secondary antibody suitable for detection.

In the method according to the invention, the so-called first TSH receptor chimeras A, B, and C can be bound to a solid phase. In this case, the binding of the TSH receptor chimeras to the solid phase can take place via an immobilizing antibody, which, for example, is directed against a C-terminal epitope of the TSH receptor chimeras. Such an antibody can be a polyclonal or monoclonal antibody.

For detection of the binding of an autoimmune antibody to one of the TSH receptor chimeras A, B, or C, a secondary antibody can be used. The secondary antibody can be present in addition to the immobilizing antibody. It can be a monoclonal or a polyclonal antibody. In such embodiments of the method according to the invention, in which the autoimmune antibody binds to protein A, G, or to anti-IgG, the Fc portion of the secondary antibody will be removed to increase the specificity and sensitivity of the assay. Thus, binding of this secondary antibody to protein A, G, or anti-IgG is avoided. The preparation of such antibodies is known and for example described in Journal of Immunological Methods, 138 (1991), 111-119. Available on the market is the ImmunoPure® F(ab'), Preparation Kit of Pierce Biotechnology Inc., Rockfort, Ill. 61105/US, as a tool for separating the Fc portion of an antibody. For this method, immobilized pepsin is used for separating the Fc portion of the antibody. A subsequent reaction with 5,5-dithiobis-(2-nitrobenzoic acid) (DTNB), followed by fusion with a peptide, which binds neither to protein A nor to protein G. Such a fusion is for example described in Science 241 (1988), 1353. The documents stated above are incorporated by reference for the purpose of description of the present invention.

The TSH receptor chimeras used according to the invention, first or second TSH receptor chimera, can be labeled depending on the desired assay design. Direct labeling within the meaning of the invention means labeling of the TSH receptor chimeras. Indirect labeling within the meaning of the invention means the use of a secondary labeled antibody. Labeling can be in such manner, that it directly or indirectly provides a detectable signal.

Labeling means can be linked with the TSH receptor chimeras or the secondary antibodies by fusion or chemical bond. Preferably, the labeling means are linked N-terminally to the TSH receptor chimera.

Suitable labeling is for example executed using enzymes like alkaline phosphatase (AP), secretory alkaline phosphatase (SEAP), glow-worm luciferase and peroxidase or a dye like an acridine dye, a fluorescent or bio/chemoluminescent material. In the case of the enzymes stated above, their encoding nucleotide sequence is preferably fused with the nucleotide sequence of the TSH receptor chimeras. Suitable labeling is further for example executed by FITC, biotinylation and streptavidin.

According to further embodiments of the method according to the invention, proteins A, G, or an anti IgG can be immobilized at a solid phase for binding an autoimmune antibody.

Suitable solid phases comprise plastic bodies like plastic tubes, plastic platelets and magnetic and non-magnetic plastic particles. Plastics suitable for the solid phases used according to the invention are such ones, which allow binding of proteins by chemical or physical reaction. These include beads, microtiter plates and tubes, which can consist of polystyrene, polyethylene or other known polymer materials. Such solid phases are known to the person skilled in the art, and are commercially available.

The truncated TSH receptor chimeras according to the invention can be stored lyophilized. They can be stored in a lyophilized form bound to a solid phase via a monoclonal or polyclonal antibody. For the detection reaction, reconstitution of the lyophilized components takes place by dissolution in an assay buffer.

The truncated TSH receptor chimeras according to the invention show high stability in their dissolved form. They remain stable at 4° C. for 4 to 7 days, at 24° C. for 3 to 6 days, and at 37° C. for 24 hours. These conditions are also suitable for the execution of the detection method according to the invention on automats, on which the components are stored at 4° C., while the test reaction can take place at 37° C. without a problem. In contrast, the complete TSH receptor chimera remains stable at 4° C. for 3 to 6 days, at 24° C. for 24 to 48 hours, and at 37° C. for only 3 hours.

In the determination of TSH auto-antibodies in the serum of patients suffering from Basedow's disease according the method of the invention, good values could be determined for the interassay variation coefficient of 4 to 12%. The intraassay precision lies clearly below 10%. The method according to the invention is excellently suitable for the automated detection of autoimmune antibodies in patient samples. For the execution of the method according to the invention, one of the three TSH receptor chimeras is added to respectively one patient sample, and the sample is then investigated for the respective autoimmune antibody.

Exemplary embodiments of the methods according to the invention are described in the following with reference to the figures.

FIG. 1 shows an embodiment of the method according to the invention, in which a truncated TSH receptor chimera bound to a solid phase has been contacted with a patient sample. An autoimmune antibody has bound to the respective epitope of the TSH receptor chimera. A second receptor chimera modified at its C-terminal end by a highly immunogenic peptide is then admixed to the reaction mixture. The second, still free epitope in the Fab portion of the patient's autoimmune antibody then binds to the second receptor chimera. The detection of the autoimmune antibody takes place with a secondary labeled antibody binding to the highly immunogenic peptide of the C-terminal end of the second TSH receptor chimera.

Figure 2:
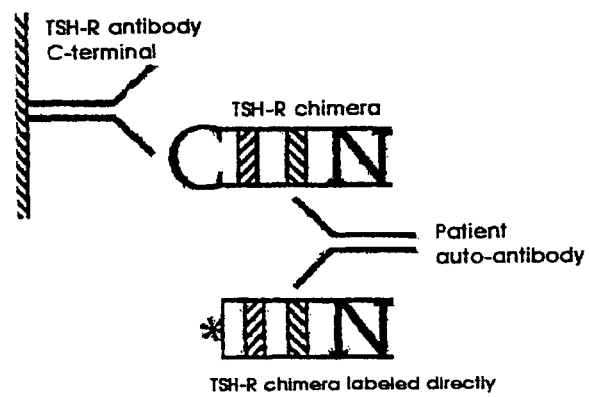
FIG. 2 shows schematically a further procedure according to the invention.

In the embodiment of FIG. 2, such a second truncated TSH receptor chimera is used, which is modified with a labeling means at its C-terminal end. In this case, no secondary labeled antibody is required.

Figure 3:
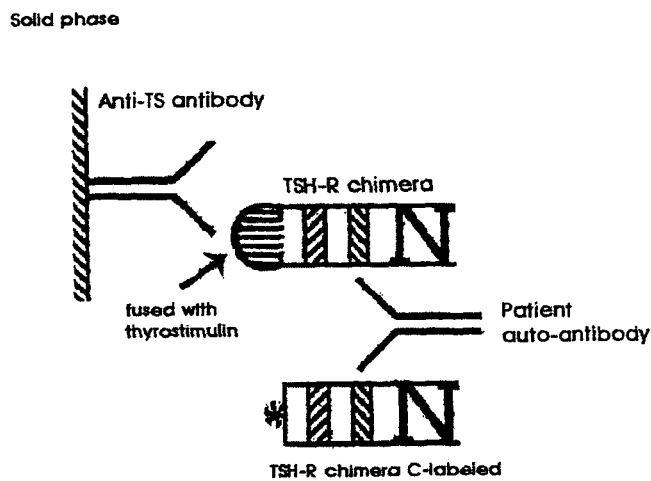
FIG. 3 shows schematically a further procedure according to the invention.

FIG. 3 shows a method, in which the immobilizing antibody is an antibody directed against the peptide thyrostimulin. The first TSH receptor chimera is a truncated receptor chimera, which at its C-terminal end is fused with the peptide thyrostimulin. The second receptor chimera likewise comprises only the extracellular portion of the receptor chimera, and is labeled at its C-terminal end. The autoimmune antibody binds to the first as well as to the second TSH receptor chimera.

Figure 4:
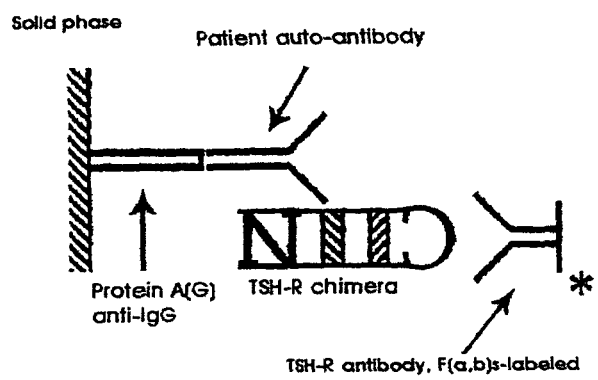
FIG. 4 shows schematically a further procedure according to the invention.

FIG. 4 shows a procedure according to the invention, in which proteins A, G, or an anti-IgG are immobilized at a solid phase, and have been contacted with a patient sample. The patient's autoimmune antibody binds with its Fc portion to proteins A, G, or anti-IgG. Following the addition of a TSH receptor chimera, the patient's autoimmune antibody binds with its Fab portion to the respective epitope of the TSH receptor chimera. For detection of the binding, a secondary labeled antibody is used, which does not have a Fc region, so that binding to proteins A, G, or anti-IgG is suppressed.

Figure 5:
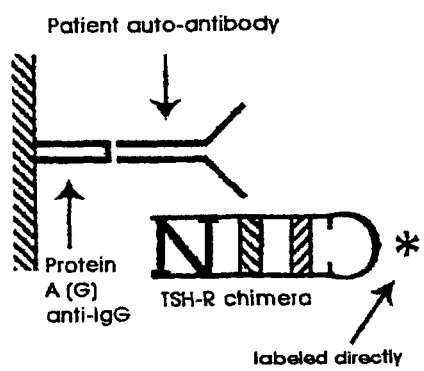
FIG. 5 shows schematically a further procedure according to the invention.

Alternatively, as shown in FIG. 5, labeling can have taken place at the C-terminal end of the TSH receptor chimera. Thus, the autoimmune antibody can be detected by a respective detection reaction with the TSH receptor chimera.

It is also possible to assay a patient sample for the presence of several TSH autoimmune antibodies. For this purpose, for example first the detection of blocking or neutral TSH autoimmune antibodies can be executed with chimeras A or C. In a further assay run, chimera B is admixed to the same patient sample, and the method according to the invention is executed.

Exemplary TSH receptor chimeras B and A according to the invention are explained in the following.

In sequence Nos. 1 and 2, respectively (TSH receptor chimera B)
  nucleotides 1 to 51 (amino acids 1 to 17) stand for the SEAP signal peptide sequence,
  nucleotides 52 to 1557 (amino acids 18 to 519) stand for the SEAP sequence,
  nucleotides 1558 to 2280 (amino acids 520 to 760) stand for the TSHR sequence of amino acids 21 to 261 of the chimera,
  nucleotides 2281 to 2298 (amino acids 760 to 766) stand for the LHR sequence of amino acids 261 to 266 of the chimera,
  nucleotides 2299 to 2316 (amino acids 767 to 772) stand for 6 histidines and TAA the stop codon.

In sequence Nos. 3 and 4, respectively (TSH receptor chimera B)
  nucleotides 1 to 60 (amino acids 1 to 20) stand for the TSHR signal peptide sequence,
  nucleotides 61 to 783 (amino acids 21 to 261) stand for the TSHR sequence of amino acids 21 to 261 of the chimera,
  nucleotides 784 to 846 (amino acids 262 to 283) stand for a highly immunogenic epitope.

In sequence Nos. 5 and 6, respectively (TSH receptor chimera A)
  nucleotides 1 to 51 (amino acids 1 to 17) stand for the SEAP signal peptide sequence,
  nucleotides 52 to 1557 (amino acids 18 to 519) stand for the SEAP sequence,
  nucleotides 1561 to 1998 (amino acids 521 to 686) stand for amino acids 21 to 166 of the LHR sequence of the chimera,
  nucleotides 1999 to 2283 (amino acids 687 to 781) stand for amino acids 166 to 370 of the TSHR sequence (between the epitopes A and B),
  nucleotides 2284 to 2553 (amino acids 782 to 891) stand for amino acids 261 to 370 of the epitope of the chimera, where blocking TSH autoimmune antibodies bind.

In sequence Nos. 7 and 8, respectively,
  nucleotides 1 to 60 (amino acids 1 to 20) stand for the TSHR/LHR signal peptide sequence,
  nucleotides 61 to 498 (amino acids 21 to 166) stand for amino acids 21 to 166 of the LHR sequence,
  nucleotides 499 to 783 (amino acids 167 to 261) stand for amino acids 166 to 370 of the TSH receptor,
  nucleotides 784 to 1113 (amino acids 262 to 371) stand for amino acids 261 to 370 of the epitope of the chimera, where blocking TSH autoimmune antibodies bind,
  nucleotides 1114 to 1176 (amino acids 372 to 392) stand for a highly immunogenic epitope from the cytosolic portion of the TSH receptor (encoded by nucleotides 743 to 763 of the TSH receptor).

In sequence Nos. 9 and 10, respectively,
nucleotides 1 to 53 (amino acids 1 to 18) stand for the gLUC signal peptide sequence,
nucleotides 54 to 561 (amino acids 19 to 187) stand for the Gaussia luciferase sequence,
nucleotides 562 to 1281 (amino acids 188 to 427) stand for amino acids 21 to 261 of the TSH receptor,
nucleotides 1282 to 1302 (amino acids 428 to 434) stand for amino acids 261 to 266 of the LHR sequence in the receptor chimera, and the remaining nucleotides for 6 histidines and the stop codon.

The invention will be further explained by the following examples.

EXAMPLES

Materials

The plasmid pcDNA3-rLHR (B9) was provided by Dr. D. L. Segaloff (The University of Iowa, USA). The plasmid pSP-luc-NF was acquired from Promega GmbH (Heidelberg, Germany). As ECL Western Blot kit and cAMP RIA kit, the kits of Amersham GmbH (Braunschweig, Germany) were used.

Used were the pIRESneo expression vector, pSEAP2-Basic of CLONTECH Laboratories, Inc., Palo Alto, Calif., USA, Gaussia luciferase of P. J. K. GmbH, Kleinbittersdorf, Germany, alkaline phosphatase *E. coli* of Laboratory voor Monoklonale Antistoffen (LMA), Wageningen, The Netherlands, horseradish peroxidase of Armoracia rusticiana, SYNTHETIC GENE, British Bio-Technology Ltd., UK, h-thyrostimulin: Nakabayashi et al., "Thyrostimulin, a heterodimer of two new human glycoprotein hormone subunits, activates the thyroid-stimulation hormone receptor", J. Clin. 109 (11), 1445-1452.

```
The DNA primers
P1  (5'-GTCATGCATCAGCTGCTGGTGCTGGCAGTG-3')
    (SEQ ID NO: 11)

P2  (5'-GTCGACGTCGTTATGTGTAAGTTATCACAG-3')
    (SEQ ID NO: 12)

P3  (5'-GTCCTTAAGAAAACACTGCCCTCCAAAGAAAAA-3')
    (SEQ ID NO: 13)

P4  (5'-ATCGAGCTCTTCATTCTCCTCAAAGATGGC-3')
    (SEQ ID NO: 14)

P5  (5'-TACGATATCGGAATGGGGTGTTCGTCT-3')
    (SEQ ID NO: 15)

P6  (5'-TATGGATCCTTATTTGGAGGGCAGTGTTTT-3')
    (SEQ ID NO: 16)

P7  (5'-TACGATATCATGCTGCTGCTGCTGCTGCTGGGC-3')
    (SEQ ID NO: 17)

P8  (5'-TACAGCGCTTGTCTGCTCGAAGCGGCC-3')
    (SEQ ID NO: 18)
``` were acquired from company Interactiva (Ulm, Germany).

Cell Culture

HEK293 cells were cultured in Dulbecco's Modified Eagle's Medium supplemented with 10% fetal bovine serum. The cells were cultivated under a 5% $CO_2$ atmosphere at 37° C.

Construction of TSHR/LH-CGR Chimeras

Three different chimeras of the human TSHR, subsequences of which were replaced by respective sequences of a rat LH-CGR, were constructed according to the description in Biochem. Biophys. Res. Commun. (1991), 179: 70-77. For one of the chimeras, hereinafter designated as "chimera A", the TSHR amino acids 8 to 165 were replaced by the comparable amino acids 10 to 166 of LH-CGR; for "chimera B", the TSHR amino acids 261 to 370 were replaced by the comparable amino acids 261 to 329 of a rat LH-CGR, while in the case of "chimera C", amino acids 8 to 165 as well as amino acids 261 to 370 were replaced by comparable LH-CGR amino acids.

In particular, the plasmid pcDNA3-rLHR (B9) was taken as the basis for that, which contains the sequence for the rat LH-CGR receptor. The DNA sequences, which encoded for amino acids 10 to 165 as well as 261 to 329, were multiplied according to the PCR technique using the primer pairs P1-P2 and P3-P4, respectively, containing NsiI, AatII, BfrI or SacI, respectively, restriction sites, whereby NsiI/AatII or BfrI/SacI-PCR, respectively, fragments were obtained. In parallel to that, a pTM1-TSHR-FLAG-6HIS plasmid, obtained according to DE 196 45 729 or Exp. Clin. Endocrinol. Diabetes 5: 282-290 (1997), was digested with PstI-AatI or BfrI-SacI restriction endonucleases. The fragments produced in that were removed and replaced by the PCR fragments obtained from the rat LH-CG receptor, whereby the cDNA sequences for the different TSHR/LH-CGR chimeras A, B, and C are obtained.

The vector pTM1-TSHR-FLAG-6HIS, or the new vector with the TSHR/LH-CGR DNA (PTM1-TSHR/LH-CGR) obtained from it, was linearized with Ava I and the "sticky" ends filled using Klenow polymerase. The vector pIRESneo was linearized with Cla I and the "sticky" ends filled using Klenow polymerase. The TSHR or TSHR/LH-CGR, respectively, fragment intended for expression, was excised using Bam HI and sub-cloned into the Cla I (filled site)/Bam I site of the expression vector pIRESneo. This results in the expression vectors pIRESneo-TSHR or pIRESneo-TSHR/LH-CGR, respectively, for cell transfection and expression of the various TSH receptor chimeras and also for modifications of the chimeras.

Preparation of the Extracellular Portion of the TSH Receptor Chimeras

The TSH receptor chimera B (wild type), cloned into the expression vector pIRESneo, is used as a template for the preparation and amplification of the nucleotide sequence with polymerase chain reaction (PCR) for the extracellular portion of the TSH receptor chimera B. The two primers required for the PCR contain the following nucleotide sequences: primer V contains a sequence of 6 nucleotides for the restriction enzyme EcoR V and a sequence of 18 nucleotides for the N-terminal peptide sequence in chimera B without a signal peptide. Primer 6 contains the nucleotide sequence for amino acids 261 to 266 together with the sequence of 6 nucleotides for Bam H1.

Insertion of the TSH Receptor Chimera B Nucleotide Sequence (Extracellular Portion Only) into Expression Vector The obtained PCR product contains the nucleotides encoding for amino acids 21 to 266. This sequence is inserted into pIRESneo via EcoR V and Bam I interfaces.

Fusion of the Nucleotide Sequences of the Extracellular TSH Receptor Chimera B and the Enzyme SEAP First, the two following primers were prepared as precondition for the subsequent fusion with pSEAP-2. Primer 7 contains the nucleotides for the N-terminal amino acid sequence of SEAP and the nucleotides for EcoR V. Primer 8 contains the nucleotides for the C-terminal amino acid sequence of SEAP together with the nucleotides of Eco 47III. Herewith, amplification of this template takes place by a polymerase chain reaction.

Insertion

Then the insertion of the fused nucleotide sequence into pIRESneo-chim B after its splitting at the EcoR V interface takes place. Using restriction analysis with the enzymes EcoR V and Bam HI, clones with the fused nucleotide sequence are selected (according to probability, 50% of the clones SEAP will be contained with the wrong orientation, which then in the restriction analysis differ from the correct fusion nucleotide sequence by a shorter length).

Incorporation of a Secretory Signal Peptide Sequence

This process takes place with the same genetic engineering methods like stated above under fusion and insertion. Here, in particular, the signal peptide sequence of transthyretin is used, since it effects a high secretion performance for the high-molecular globulin transthyretin.

Expression and Collection of Fusion Proteins TSHR-SEAP and TSHR/LH-CGR-SEAP, Respectively, as a Cell Extract Confluent stable HEK293 cells are cultured in 10 to 20 75 $cm^2$ plates (approx. 20×106 cells). After scraping off, the cells are transferred into phosphate-buffered saline solution (PBS), and washed four times with PBS under centrifugation at 2500 rpm. The cells obtained were lysed in 0.3 ml of a buffer A (20 mM Hepes-KOH; pH 7.5; 50 mM NaCl; 1% Triton X100; 10% glycerol) under freezing and thawing. The suspension obtained was centrifuged at 30,000 G for 1 hour, the supernatant (approx. 8 mg/ml of total protein) was collected and stored at −70° C.

The supernatant obtained in that manner (extract) can be used in determination methods as TSHR-SEAP or TSHR/LH-CGR-SEAP, respectively.

Preparation of Cell Fractions

The HEK193 cells were pelletized by centrifugation at 1,200 rpm. The cell pellet obtained was re-suspended in 0.3 ml of a buffer, which contained in 10 mM Tris-HCl, pH 7.6, 50 mM NaCl, 10% glycerol as well as a protease inhibitor mixture. The suspension was then homogenized at 4° C. by 20 stroke movements in a glass-teflon homogenizer, and then centrifuged for 15 min. at 800 G, and subsequently for 1 hour at 30,000 G. The supernatant (the cytoplasma fraction) was collected. The membrane pellet was processed by homogenizing it at 4° C. by 20 stroke movements in a glass-teflon homogenizer in 0.3 ml of 1% triton X100 in the same buffer, and then centrifuging it at 30,000 G for 1 hour. The supernatant (triton X100 membrane extract) was collected and stored at −70° C.

Collection of the Secreted Extracellular Fusion TSHR Chimeras

The truncated, extracellular domains of the fusion TSH-R chimeras are secreted into the culture supernatant by the cells expressing them. The secreted receptor proteins are directly used in the assay in the form of certain dilutions in the assay buffer. For example, 10 μl of extracellular SEAP-TSH-R chimera B from 5 ml of culture supernatant are used in a final dilution of 1:10 per determination.

Generation of a Standard Calibration Curve

For the generation of a standard curve, a standard solution WHO 90/672 with a standardized concentration of autoimmune antibody was used. The initial solution of the standard contains 100 IU/l, which were diluted for the purposes of generation of the standard curve. As zero value, the serum of a subject without autoimmune antibody in TXBW buffer was used.

The TSH receptor chimeras B used are stored lyophilized on microtiter plates fixed via antibody, and are reconstituted in buffer with protein stabilizers before their use. The triton X100 wash buffer (TXWB) contains 0.1% TX-100, 50 mM Tris/HCl pH 8.0, 100 mM NaCl. The serum dilution buffer contains 5% glucose and 5% milk powder in TXWB.

50 μl of sample solution (dilutions of the standard and zero sample) per cavity are diluted with dilution buffer 1:2 and incubated on microtiter plates at room temperature (approx. 22° C.) for 90 minutes. Four washings take place with 300 μl of TXWB each. Then 10 μl of a 1:100 dilution from 5 ml of culture supernatant of a culture dish with a diameter of 10 cm of extracellular TSH receptor chimera, fused with an enzyme SEAP, are added to 90 μl of TXWB. Subsequently, incubation takes place under agitation (300 to 400 rpm) at 37° C. for 30 minutes. Then four washings take place with 300 μl of TXWB. The bio/chemo-luminescence is measured with the Centrol® IA LB 296 microtiter plate measuring device of Berthold GmbH, Bad Wildbad, Schwarzwald, Germany, using Tropix® (reagent for ECL (enhanced chemo-luminescence)) of Applied Biosystems, Foster City, Calif., USA.

The detection limit is approx. 0.2 IU/l. There exists a polynomial function between relative light units (RLU) and the concentrations of the standard for stimulating auto-antibodies over an area ranging up to at least 40 IU/l.

Figure 6:
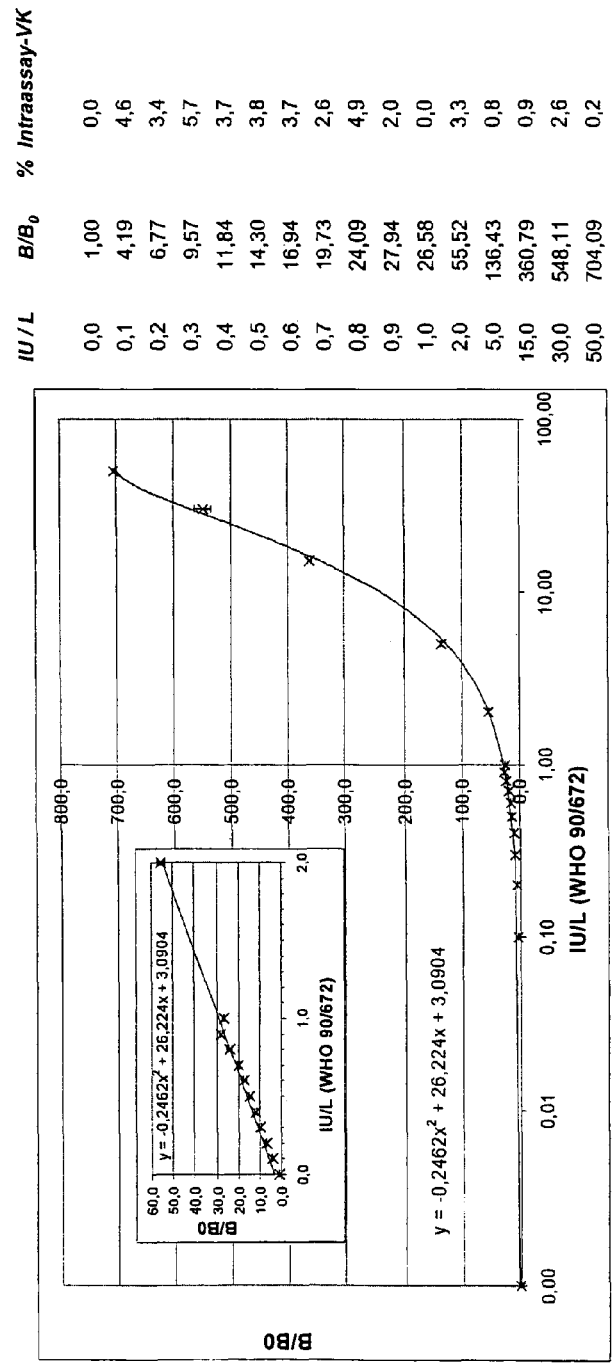
FIG. 6 shows a standard curve with NIBSC (WHO) standard solutions of TSH autoimmune antibodies obtained-according to the method of the invention.
Figure 7:
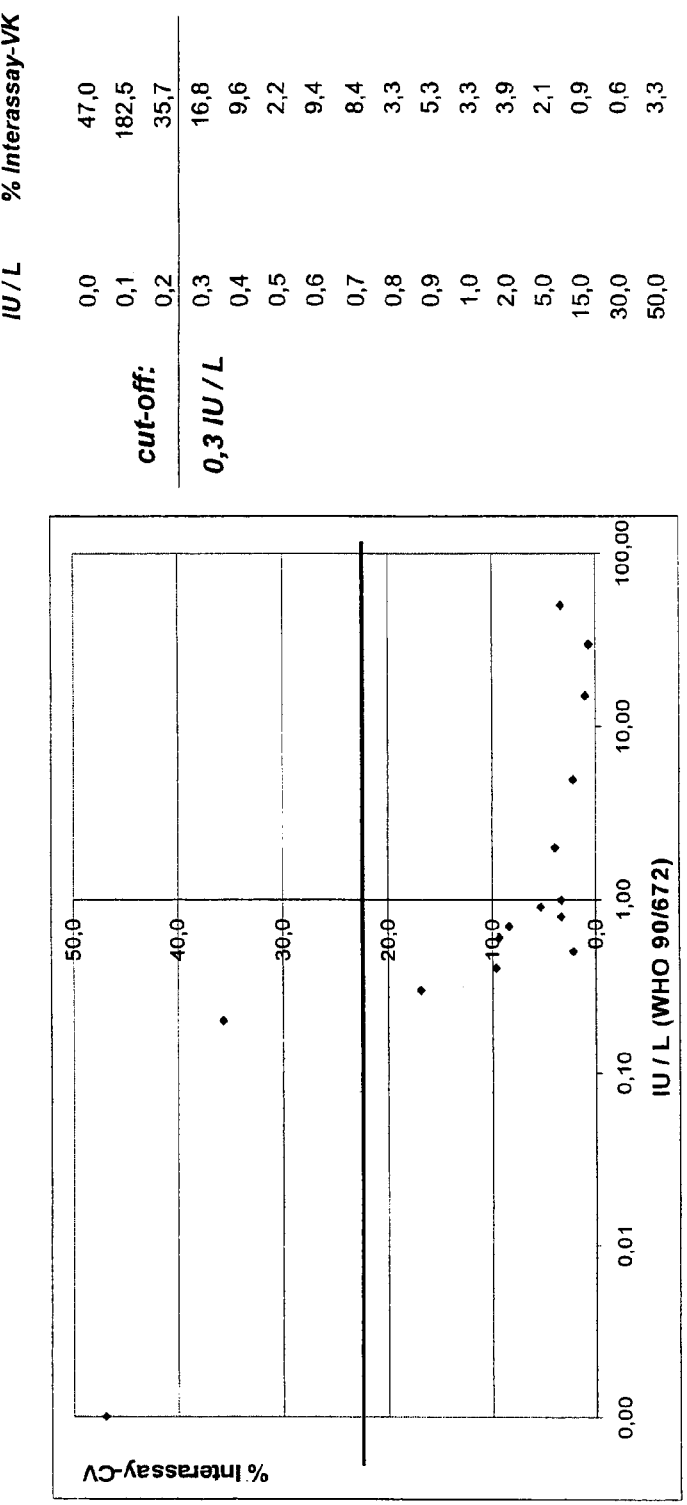
FIG. 7 shows an interassay precision profile, generated with the WHO standard 90/672 at n=5 from triple determinations per assay.

In FIG. 6, the relation of the relative light unit (RLU) of the RLU (B=bound) measured in the samples of the dilution series of the TSH receptor auto-antibody standard respectively in relation to the zero value of a subject without autoimmune antibody (B0) is shown on the Y-axis as B/B0. On the X-axis, the dilution of the standard samples is stated. The measurement values, averages from double determinations, are shown in the following table.

| IU/L | Dilution factor NIBSC (100 IU/L) | RLU Average n = 3 | B/B0 | Intraassay variation coefficient |
|---|---|---|---|---|
| 0.0 | — | 6,882.3 | 1.00 | 0.0 |
| 0.1 | 1000 | 28,847.7 | 4.19 | 4.6 |
| 0.2 | 500 | 46,607.0 | 6.77 | 3.4 |
| 0.3 | 333.3 | 65,848.3 | 9.57 | 5.7 |
| 0.4 | 250 | 81,488.0 | 11.84 | 3.7 |
| 0.5 | 200 | 98,427.3 | 14.30 | 3.8 |
| 0.6 | 166.7 | 116,567.7 | 16.94 | 3.7 |
| 0.7 | 142.9 | 135,783.7 | 19.73 | 2.6 |
| 0.8 | 125 | 165,778.3 | 24.09 | 4.9 |
| 0.9 | 111.1 | 192,274.7 | 27.94 | 2.0 |
| 1.0 | 100 | 182,910.3 | 26.58 | 0.0 |
| 2.0 | 50 | 382,131.7 | 55.52 | 3.3 |
| 5.0 | 20 | 938,959.7 | 136.43 | 0.8 |
| 15.0 | 6.7 | 2,483,045.7 | 360.79 | 0.9 |
| 30.0 | 3.3 | 3,772,245.0 | 548.11 | 2.6 |
| 50.0 | 2 | 4,845,780.7 | 704.09 | 0.2 |

Comparison of the Assay According to the Invention with the Competition Assay of the "Second Generation"

Serum or plasma samples are extracted from venous blood within 3 hours. Storage is possible at 4° C. over a period of 7 days or at −20° C. for 1 to 2 years. Secondary antibodies (see above) are stored at −20° C., and thawed at room temperature before their use in the assay. TSH receptor chimeras are stored lyophilized on microtiter plates, and reconstituted in buffer with protein stabilizers before their use. Triton X100 wash buffer (TXWB) contains 0.1% TX-100, 50 mM Tris/HCl pH 8.0, 100 ml NaCl. Serum dilution buffer contains 5% glucose and 5% milk powder in TXWB.

50 μl of serum or plasma per cavity are diluted with buffer TXWB 1:2, and incubated on microtiter plates at room temperature (approx. 22° C.) for 90 minutes. Then 10 μl of a 1:10 dilution of 5 ml of culture supernatant of a culture dish with a diameter of 10 cm of extracellular TSH receptor chimera, fused with an enzyme SEAP, are added to 90 µl of TXWB. Subsequently, incubation takes place under agitation (300 to 400 rpm) at 37° C. for 30 minutes. Then four washings take place with 300 µl of TXWB. The bio/chemo-luminescence is measured with the Centrol® IA LB 296 microtiter plate measuring device using Tropix®.

Figure 8:
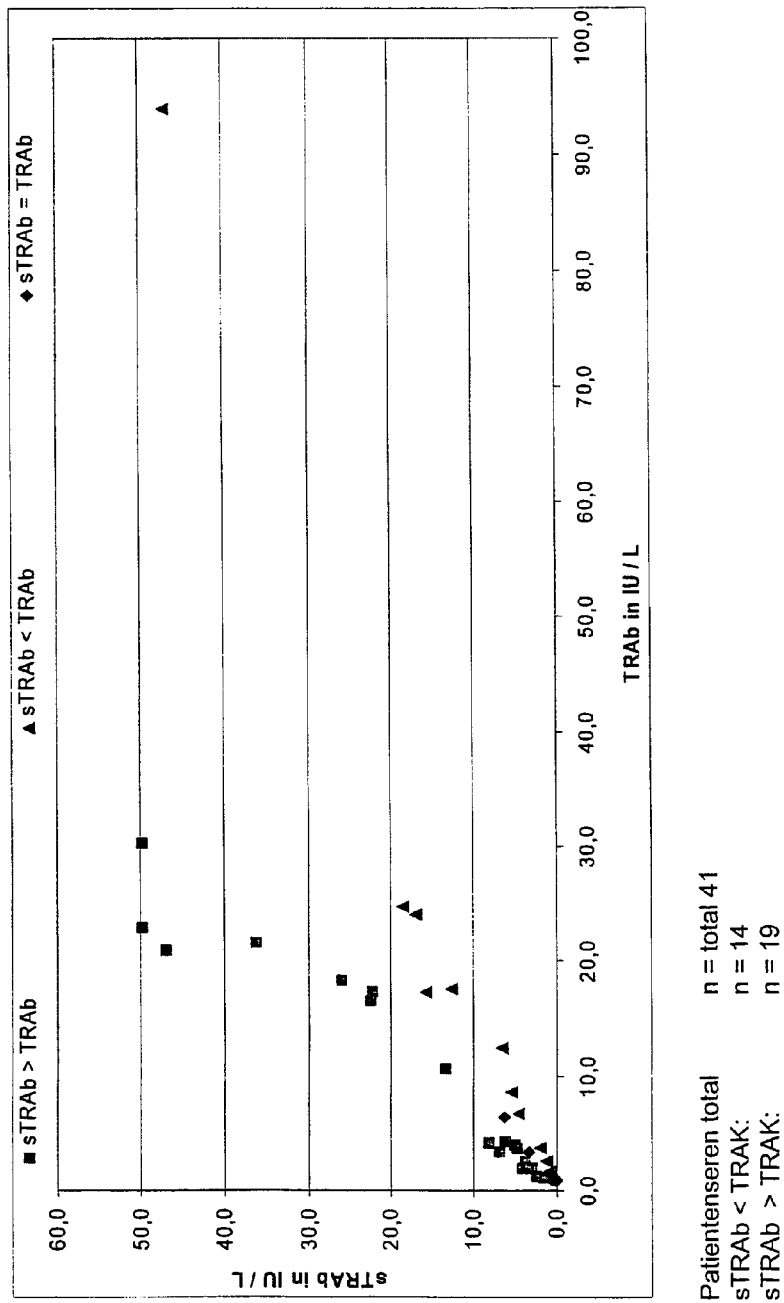
FIG. 8 shows a comparison of the measuring results produced with patient serums with the method according to the invention and with an assay of the so-called second generation.

FIG. 8 shows by way of comparison the measurement results achieved with patient serums using the method according to the invention and using an assay of the so-called second generation. In the second-generation assay, a complete TSH receptor—no receptor chimera—was used in a competition assay. For that, the TSH receptor is immobilized at a solid phase and contacted with sample serum and labeled TSH. The concentration of the TSH used was varied. Autoimmune antibodies displace TSH from the receptor. The signal change effected by the displacement is used as measurement value.

The analysis design of the assay according to the invention was that of FIG. 2. The execution of the competition assay took place according to the instructions of the assay kit TRAK® of B.R.A.H.M.S. AG, 16761 Hennigsdorf, Germany, which was used.

In FIG. 8, the international units per liter determined according to the invention are stated on the Y-axis, and those according to the second-generation method on the X-axis of the diagram. The analysis shows, that for a total of 41 patient serums the sTRAb values are lower than the TRAK values in 14 cases, and higher in 19 cases.

Although the invention was described above with reference to certain embodiments, changes and modifications are possible, which are apparent for the person skilled in the art and which do not exceed the scope of the patent determined by the claims.

The invention claimed is:

1. A method for determination of stimulating autoimmune antibodies directed against the thyroid-stimulating hormone (TSH) receptor in a patient sample, using TSH receptor chimera B, wherein the amino acids from 261 to 370 of the TSH receptor are replaced by the comparable amino acids from 261 to 329 of a rat LH-CGR said method comprising:
   (a) contacting a patient sample that is to be tested for a stimulating autoimmune antibody with a first receptor chimera wherein said first receptor chimera B is a holoreceptor chimera is bound to a solid phase, and wherein said stimulating autoimmune antibody comprises a first antigen-binding site and a second antigen-binding site;
   (b) allowing binding of said stimulating autoimmune antibody first antigen-binding site with said first receptor chimera B;
   (c) adding a second receptor chimera B, wherein said second receptor chimera B is a truncated chimera B, wherein said truncated chimera B comprises only the extracellular domain of said first receptor chimera B, and wherein said second receptor chimera B is modified at its C-terminal end or N-terminal end to allow for the detection of said second receptor chimera B;
   (d) allowing binding of said stimulating autoimmune antibody second antigen-binding site to said second receptor chimera B; and
   (e) determining if a stimulating autoimmune antibody is present in said patient sample.

2. The method according to claim 1, wherein said first receptor chimera B is bound to said solid phase by an immobilized antibody, and said second receptor chimera B does not bind to said immobilized antibody.

3. The method according to claim 2, wherein said second receptor chimera B is modified at its C-terminal end by fusion to a peptide that is recognized by a secondary antibody suitable for detection.

4. The method according to claim 3, wherein said peptide is a subsequence from thyrostimulin.

5. The method according to claim 2, wherein said second receptor chimera B is modified at its C-terminal end with a label suitable for detection.

6. The method according to claim 2, wherein said first receptor chimera B is modified at its C-terminal end by fusion to a peptide that is recognized by said immobilized antibody.

7. The method according to claim 6, wherein the peptide is a subsequence from thyrostimulin.

8. The method according to claim 5, wherein said label is an acridine compound, a ruthenium compound, biotin, streptavidin or fluorescein isothiocyanate.

9. The method according to claim 5, wherein said label is a secretory alkaline phosphatase, a glowworm luciferase, a Gaussia luciferase, or a peroxidase.

10. The method according to claim 1, wherein the second receptor chimera B is modified at its C-terminal end.

11. The method according to claim 1, wherein the second receptor B chimera is modified at its N-terminal end.

12. The method according to claim 2, wherein the second receptor chimera B is modified at its N-terminal end by fusion to a peptide that is recognized by a secondary antibody suitable for detection.

13. The method according to claim 12, wherein said peptide is a subsequence from thyrostimulin.

14. The method according to claim 2, wherein said second receptor chimera B is modified at its C-terminal end by fusion to an enzyme.

15. The method of claim 14, wherein said enzyme is alkaline phosphatase, secretory alkaline phosphatase, a glow-worm luciferase, a Gaussia luciferase, or a peroxidase.

16. The method according to claim 2, wherein said second receptor chimera B is modified at its N-terminal end by fusion to an enzyme.

17. The method of claim 16, wherein said enzyme is alkaline phosphatase, secretory alkaline phosphatase, a glow-worm luciferase, a Gaussia luciferase, or a peroxidase.

* * * * *

SEQUENCE LISTING

```
<160> NUMBER OF SEQ ID NOS: 18

<210> SEQ ID NO 1
<211> LENGTH: 2319
<212> TYPE: DNA
<213> ORGANISM: Homo sapiens

<400> SEQUENCE: 1
atgctgctgc tgctgctgct gctgggcctg aggctacagc tctccctggg catcatccca      60
gttgaggagg agaacccgga cttctggaac cgcgaggcag ccgaggccct gggtgccgcc     120
aagaagctgc agcctgcaca gacagccgcc aagaacctca tcatcttcct gggcgatggg     180 atggggggtgt ctacggtgac agctgccagg atcctaaaag ggcagaagaa ggacaaactg     240
gggcctgaga taccoctggc catggaccgc ttcccatatg tggctctgtc caagacatac     300
aatgtagaca aacatgtgcc agacagtgga gccacagcca cggcctacct gtgcggggtc     360
aagggcaact tccagaccat tggcttgagt gcagccgccc gctttaacca gtgcaacacg     420
acacgcggca acgaggtcat ctccgtgatg aatcgggcca agaaagcagg gaagtcagtg     480
ggagtggtaa ccaccacacg agtgcagcac gcctcgccag ccggcaccta cgcccacacg     540
gtgaaccgca actggtactc ggacgccgac gtgcctgcct cggcccgcca ggaggggtgc     600
caggacatcg ctacgcagct catctccaac atggacattg acgtgatcct aggtggaggc     660
cgaaagtaca tgttccgcat gggaaccca gaccctgagt acccagatga ctacagccaa     720
ggtgggacca ggctggacgg gaagaatctg gtgcaggaat ggctggcgaa gcgccagggt     780
gcccggtatg tgtggaaccg cactgagctc atgcaggctt ccctggaccc gtctgtgacc     840
catctcatgg gtctctttga gcctggagac atgaaatacg agatccaccg agactccaca     900 ctggaccct ccctgatgga gatgacagag gctgccctgc gcctgctgag caggaacccc     960
cgcggcttct tcctcttcgt ggagggtggt cgcatcgacc atggtcatca tgaaagcagg    1020
gcttaccggg cactgactga gacgatcatg ttcgacgacg ccattgagag ggcgggccag    1080
ctcaccagcg aggaggacac gctgagcctc gtcactgccg accactccca cgtcttctcc    1140
ttcggaggct acccctgcg agggagctcc atcttcgggc tggcccctgg caaggcccgg    1200
gacaggaagg cctacacggt cctcctatac ggaaacggtc aggctatgt gctcaaggac    1260 ggcgcccggc cggatgttac cgagagcgag agcgggagcc ccgagtatcg gcagcagtca    1320
gcagtgcccc tggacgaaga gacccacgca ggcgaggacg tggcggtgtt cgcgcgcggc    1380
ccgcaggcgc acctggttca cggcgtgcag gagcagacct tcatagcgca cgtcatggcc    1440
```

```
ttcgccgcct gcctggagcc ctacaccgcc tgcgacctgg cgcccccgc cggcaccacc   1500 gacgccgcgc acccgggtta ctctagagtc ggggcggccg gccgcttcga gcagacagga   1560
atggggtgtt cgtctccacc ctgcgagtgc catcaggagg aggacttcag agtcacctgc   1620
aaggatattc aacgcatccc cagcttaccg cccagtacgc agactctgaa gcttattgag   1680
actcacctga gaactattcc aagtcatgca ttttctaatc tgcccaatat ttccagaatc   1740
tacgtatcta tagatgtgac tctgcagcag ctggaatcac actccttcta caatttgagt   1800
aaagtgactc acatagaaat tcggaatacc aggaacttaa cttacataga ccctgatgcc   1860
ctcaaagagc tccccctcct aaagttcctt ggcattttca acactggact taaaatgttc   1920
cctgacctga ccaaagttta ttccactgat atattcttta acttgaaat tacagacaac   1980 ccttacatga cgtcaatccc tgtgaatgct tttcagggac tatgcaatga aaccttgaca   2040
ctgaagctgt acaacaatgg ctttacttca gtccaaggat atgctttcaa tgggacaaag   2100
ctggatgctg tttacctaaa caagaataaa tacctgacag ttattgacaa agatgcattt   2160
ggaggagtat acagtggacc aagcttgctg acgtgtctc aaaccagtgt cactgcccttt   2220 ccatccaaag gcctggagca cctgaaggaa ctgatagcaa gaaacacctg gactcttaag   2280
aaaacactgc cctccaaaca tcaccatcac catcactaa                         2319
```

<210> SEQ ID NO 2
<211> LENGTH: 772
<212> TYPE: PRT
<213> ORGANISM: Homo sapiens

<400> SEQUENCE: 2

```
Met Leu Leu Leu Leu Leu Leu Gly Leu Arg Leu Gln Leu Ser Leu
1               5                   10                  15

Gly Ile Ile Pro Val Glu Glu Asn Pro Asp Phe Trp Asn Arg Glu
                20                  25                  30

Ala Ala Glu Ala Leu Gly Ala Ala Lys Lys Leu Gln Pro Ala Gln Thr
            35                  40                  45

Ala Ala Lys Asn Leu Ile Ile Phe Leu Gly Asp Gly Met Gly Val Ser
        50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
    130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
        195                 200                 205

Ser Asn Met Asp Ile Asp Val Ile Leu Gly Gly Gly Arg Lys Tyr Met
```

```
                    210                 215                 220
Phe Arg Met Gly Thr Pro Asp Pro Glu Tyr Pro Asp Tyr Ser Gln
225                 230                 235                 240

Gly Gly Thr Arg Leu Asp Gly Lys Asn Leu Val Gln Glu Trp Leu Ala
                245                 250                 255

Lys Arg Gln Gly Ala Arg Tyr Val Trp Asn Arg Thr Glu Leu Met Gln
                260                 265                 270

Ala Ser Leu Asp Pro Ser Val Thr His Leu Met Gly Leu Phe Glu Pro
                275                 280                 285

Gly Asp Met Lys Tyr Glu Ile His Arg Asp Ser Thr Leu Asp Pro Ser
290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
                340                 345                 350

Asp Ala Ile Glu Arg Ala Gly Gln Leu Thr Ser Glu Glu Asp Thr Leu
                355                 360                 365

Ser Leu Val Thr Ala Asp His Ser His Val Phe Ser Phe Gly Gly Tyr
370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
                420                 425                 430

Ser Pro Glu Tyr Arg Gln Gln Ser Ala Val Pro Leu Asp Glu Glu Thr
                435                 440                 445

His Ala Gly Glu Asp Val Ala Val Phe Ala Arg Gly Pro Gln Ala His
                450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly Tyr Ser Arg Val Gly Ala
                500                 505                 510

Ala Gly Arg Phe Glu Gln Thr Gly Met Gly Cys Ser Ser Pro Pro Cys
                515                 520                 525

Glu Cys His Gln Glu Glu Asp Phe Arg Val Thr Cys Lys Asp Ile Gln
                530                 535                 540

Arg Ile Pro Ser Leu Pro Ser Thr Gln Thr Leu Lys Leu Ile Glu
545                 550                 555                 560

Thr His Leu Arg Thr Ile Pro Ser His Ala Phe Ser Asn Leu Pro Asn
                565                 570                 575

Ile Ser Arg Ile Tyr Val Ser Ile Asp Val Thr Leu Gln Gln Leu Glu
                580                 585                 590

Ser His Ser Phe Tyr Asn Leu Ser Lys Val Thr His Ile Glu Ile Arg
                595                 600                 605

Asn Thr Arg Asn Leu Thr Tyr Ile Asp Pro Asp Ala Leu Lys Glu Leu
                610                 615                 620

Pro Leu Leu Lys Phe Leu Gly Ile Phe Asn Thr Gly Leu Lys Met Phe
625                 630                 635                 640
```

Pro Asp Leu Thr Lys Val Tyr Ser Thr Asp Ile Phe Phe Ile Leu Glu
              645                 650                 655

Ile Thr Asp Asn Pro Tyr Met Thr Ser Ile Pro Val Asn Ala Phe Gln
          660                 665                 670

Gly Leu Cys Asn Glu Thr Leu Thr Leu Lys Leu Tyr Asn Asn Gly Phe
      675                 680                 685

Thr Ser Val Gln Gly Tyr Ala Phe Asn Gly Thr Lys Leu Asp Ala Val
  690                 695                 700

Tyr Leu Asn Lys Asn Lys Tyr Leu Thr Val Ile Asp Lys Asp Ala Phe
705                 710                 715                 720

Gly Gly Val Tyr Ser Gly Pro Ser Leu Leu Asp Val Ser Gln Thr Ser
              725                 730                 735

Val Thr Ala Leu Pro Ser Lys Gly Leu Glu His Leu Lys Glu Leu Ile
              740                 745                 750

Ala Arg Asn Thr Trp Thr Leu Lys Lys Thr Leu Pro Ser Lys His His
          755                 760                 765

His His His His
    770

<210> SEQ ID NO 3
<211> LENGTH: 849
<212> TYPE: DNA
<213> ORGANISM: Homo sapiens

<400> SEQUENCE: 3

```
atgaggccgg cggacttgct gcagctggtg ctgctgctcg acctgcccag ggacctgggc    60
ggaatggggt gttcgtctcc accctgcgag tgccatcagg aggaggactt cagagtcacc   120
tgcaaggata ttcaacgcat ccccagctta ccgcccagta cgcagactct gaagcttatt   180
gagactcacc tgagaactat tccaagtcat gcattttcta atctgcccaa tatttccaga   240
atctacgtat ctatagatgt gactctgcag cagctggaat cacactcctt ctacaatttg   300
agtaaagtga ctcacataga aattcggaat accaggaact taacttacat agaccctgat   360
gccctcaaag agctccccct cctaaagttc cttggcattt tcaacactgg acttaaaatg   420
ttccctgacc tgaccaaagt ttattccact gatatattct ttatacttga aattacagac   480
aacccttaca tgacgtcaat ccctgtgaat gcttttcagg gactatgcaa tgaaaccttg   540
acactgaagc tgtacaacaa tggctttact tcagtccaag gatatgcttt caatgggaca   600
aagctggatg ctgtttacct aaacaagaat aaatacctga cagttattga caaagatgca   660
tttggaggag tatacagtgg accaagcttg ctggacgtgt ctcaaaccag tgtcactgcc   720
cttccatcca aaggcctgga gcacctgaag gaactgatag caagaaacac ctggactctt   780
aaggaaaaat cccatctaac cccaaagaag caaggccaaa tctcagaaga gtatatgcaa   840
acggtttaa                                                           849
```

<210> SEQ ID NO 4
<211> LENGTH: 282
<212> TYPE: PRT
<213> ORGANISM: Homo sapiens

<400> SEQUENCE: 4

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Cys Glu Cys His
            20                  25                  30

```
Gln Glu Glu Asp Phe Arg Val Thr Cys Lys Asp Ile Gln Arg Ile Pro
         35                  40                  45
Ser Leu Pro Pro Ser Thr Gln Thr Leu Lys Leu Ile Glu Thr His Leu
 50                  55                  60
Arg Thr Ile Pro Ser His Ala Phe Ser Asn Leu Pro Asn Ile Ser Arg
 65                  70                  75                  80
Ile Tyr Val Ser Ile Asp Val Thr Leu Gln Gln Leu Glu Ser His Ser
                 85                  90                  95
Phe Tyr Asn Leu Ser Lys Val Thr His Ile Glu Ile Arg Asn Thr Arg
             100                 105                 110
Asn Leu Thr Tyr Ile Asp Pro Asp Ala Leu Lys Glu Leu Pro Leu Leu
         115                 120                 125
Lys Phe Leu Gly Ile Phe Asn Thr Gly Leu Lys Met Phe Pro Asp Leu
 130                 135                 140
Thr Lys Val Tyr Ser Thr Asp Ile Phe Phe Ile Leu Glu Ile Thr Asp
145                 150                 155                 160
Asn Pro Tyr Met Thr Ser Ile Pro Val Asn Ala Phe Gln Gly Leu Cys
                 165                 170                 175
Asn Glu Thr Leu Thr Leu Lys Leu Tyr Asn Asn Gly Phe Thr Ser Val
             180                 185                 190
Gln Gly Tyr Ala Phe Asn Gly Thr Lys Leu Asp Ala Val Tyr Leu Asn
         195                 200                 205
Lys Asn Lys Tyr Leu Thr Val Ile Asp Lys Asp Ala Phe Gly Gly Val
 210                 215                 220
Tyr Ser Gly Pro Ser Leu Leu Asp Val Ser Gln Thr Ser Val Thr Ala
225                 230                 235                 240
Leu Pro Ser Lys Gly Leu Glu His Leu Lys Glu Leu Ile Ala Arg Asn
                 245                 250                 255
Thr Trp Thr Leu Lys Glu Lys Ser His Leu Thr Pro Lys Lys Gln Gly
             260                 265                 270
Gln Ile Ser Glu Glu Tyr Met Gln Thr Val
         275                 280

<210> SEQ ID NO 5
<211> LENGTH: 2615
<212> TYPE: DNA
<213> ORGANISM: Homo sapiens

<400> SEQUENCE: 5
atgctgctgc tgctgctgct gctgggcctg aggctacagc tctccctggg catcatccca      60
gttgaggagg agaacccgga cttctggaac cgcgaggcag ccgaggccct gggtgccgcc     120
aagaagctgc agcctgcaca gacagccgcc aagaacctca tcatcttcct gggcgatggg     180 atggggtgt ctacggtgac agctgccagg atcctaaaag gcagaagaa ggacaaactg      240 gggcctgaga taccctggc catgaccgc ttcccatatg tggctctgtc caagacatac       300
aatgtagaca acatgtgcc agacagtgga gccacagcca cggcctacct gtgcggggtc      360
aagggcaact tccagaccat tggcttgagt gcagccgccc gctttaacca gtgcaacacg     420
acacgcggca cgaggtcat ctccgtgatg aatcgggcca agaaagcagg gaagtcagtg      480
ggagtggtaa ccaccacacg agtgcagcac gcctcgccag ccggcaccta cgcccacacg     540
gtgaaccgca actggtactc ggacgccgac gtgcctgcct cggcccgcca ggagggtgc     600 aggacatcgc tacgcagctc atctccaaca tggacattga cgtgatccta ggtggaggcc     660
```

```
gaaagtacat gtttcgcatg ggaaccccag accctgagta cccagatgac tacagccaag    720
gtgggaccag gctggacggg aagaatctgg tgcaggaatg gctggcgaag cgccagggtg    780
cccggtatgt gtggaaccgc actgagctca tgcaggcttc cctggacccg tctgtgaccc    840
atctcatggg tctctttgag cctggagaca tgaaatacga gatccaccga gactccacac    900
tggacccctc cctgatggag atgacagagg ctgccctgcg cctgctgagc aggaaccccc    960
gcggcttctt cctcttcgtg gagggtggtc gcatcgacca tggtcatcat gaaagcaggg   1020
cttaccgggc actgactgag acgatcatgt tcgacgacgc cattgagagg gcgggccagc   1080
tcaccagcga ggaggacacg ctgagcctcg tcactgccga ccactcccac gtcttctcct   1140
tcggaggcta ccccctgcga gggagctcca tcttcgggct ggcccctggc aaggcccggg   1200
acaggaaggc ctacacggtc ctcctatacg gaaacggtcc aggctatgtg ctcaaggacg   1260
gcgcccggcc ggatgttacc gagagcgaga gcggagcccc gagtatcgg cagcagtcag    1320
cagtgcccct ggacgaagag acccacgcag gcgaggacgt ggcggtgttc gcgcgcggcc   1380
cgcaggcgca cctggttcac ggcgtgcagg agcagacctt catagcgcac gtcatggcct   1440
tcgccgcctg cctggagccc tacaccgcct gcgacctggc gccccccgcc ggcaccaccg   1500
acgccgcgca cccgggttac tctagagtcg gggcggccgg ccgcttcgag cagacaaagc   1560
cttcacagct gcagtcccga gagctgtcag ggtcgcgctg ccccgagccc tgcgactgcg   1620
caccggatgg cgccctgcgc tgtcctggcc ctcgagccgg cctcgccaga ctatctctca   1680
cctatctccc tgtcaaagta attccatcac aagctttcag gggacttaat gaggtcgtaa   1740
aaattgaaat ctctcagagt gattccctgg aaaggataga agctaatgcc tttgacaacc   1800
tcctcaattt gtctgaacta ctgatccaga acaccaaaaa cctgctatac attgaacctg   1860
gtgcttttac aaacctccct cggttaaaat acctgagcat ctgtaacaca ggcatccgaa   1920
cccttccaga tgttacgaag atctcctcct ctgaatttaa tttcattctg gaaatctgtg   1980
ataacttaca cataacctca atccctgtga atgcttttca gggactatgc aatgaaacct   2040
tgacactgaa gctgtacaac aacggcttta cttcagtcca aggatatgct ttcaatggga   2100
caaagctgga tgctgtttac ctaaacaaga ataaatacct gacagttatt gacaaagatg   2160
catttggagg agtatacagt ggaccaagct tgctggacgt gtctcaaacc agtgtcactg   2220
cccttccatc caaaggcctg gagcacctga aggaactgat agcaagaaac acctggactc   2280
ttaagaaact tccactttcc ttgagtttcc ttcacctcac acgggctgac cttcttacc    2340
caagccactg ctgtgccttt aagaatcaga gaaaatcag aggaatcctt gagtccttga    2400
tgtgtaatga gagcagtatg cagagcttgc gccagagaaa atctgtgaat gccttgaata    2460
gcccctcca ccaggaatat gaagagaatc tgggtgacag cattgttggg tacaaggaaa    2520
agtccaagtt ccaggatact cataacaacg ctcattatta cgtcttcttt gaagaacaag    2580
aggatgagat cattggtttt ggccaggagc tctaa                              2615
```

<210> SEQ ID NO 6
<211> LENGTH: 871
<212> TYPE: PRT
<213> ORGANISM: Homo sapiens

<400> SEQUENCE: 6

```
Met Leu Leu Leu Leu Leu Leu Gly Leu Arg Leu Gln Leu Ser Leu
1               5                   10                  15

Gly Ile Ile Pro Val Glu Glu Glu Asn Pro Asp Phe Trp Asn Arg Glu
            20                  25                  30
```

-continued

Ala Ala Glu Ala Leu Gly Ala Ala Lys Lys Leu Gln Pro Ala Gln Thr
         35                  40                  45

Ala Ala Lys Asn Leu Ile Ile Phe Leu Gly Asp Gly Met Gly Val Ser
 50                  55                  60

Thr Val Thr Ala Ala Arg Ile Leu Lys Gly Gln Lys Lys Asp Lys Leu
 65              70                  75                      80

Gly Pro Glu Ile Pro Leu Ala Met Asp Arg Phe Pro Tyr Val Ala Leu
                 85                  90                  95

Ser Lys Thr Tyr Asn Val Asp Lys His Val Pro Asp Ser Gly Ala Thr
                100                 105                 110

Ala Thr Ala Tyr Leu Cys Gly Val Lys Gly Asn Phe Gln Thr Ile Gly
             115                 120                 125

Leu Ser Ala Ala Ala Arg Phe Asn Gln Cys Asn Thr Thr Arg Gly Asn
130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
             180                 185                 190

Ala Ser Ala Arg Gln Glu Gly Cys Gln Asp Ile Ala Thr Gln Leu Ile
         195                 200                 205

Ser Asn Met Asp Ile Asp Val Ile Leu Gly Gly Gly Arg Lys Tyr Met
210                 215                 220

Phe Arg Met Gly Thr Pro Asp Pro Glu Tyr Pro Asp Asp Tyr Ser Gln
225                 230                 235                 240

Gly Gly Thr Arg Leu Asp Gly Lys Asn Leu Val Gln Glu Trp Leu Ala
                245                 250                 255

Lys Arg Gln Gly Ala Arg Tyr Val Trp Asn Arg Thr Glu Leu Met Gln
             260                 265                 270

Ala Ser Leu Asp Pro Ser Val Thr His Leu Met Gly Leu Phe Glu Pro
         275                 280                 285

Gly Asp Met Lys Tyr Glu Ile His Arg Asp Ser Thr Leu Asp Pro Ser
290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
             340                 345                 350

Asp Ala Ile Glu Arg Ala Gly Gln Leu Thr Ser Glu Glu Asp Thr Leu
         355                 360                 365

Ser Leu Val Thr Ala Asp His Ser His Val Phe Ser Phe Gly Gly Tyr
370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
             420                 425                 430

Ser Pro Glu Tyr Arg Gln Gln Ser Ala Val Pro Leu Asp Glu Glu Thr
         435                 440                 445

-continued

His Ala Gly Glu Asp Val Ala Val Phe Ala Arg Gly Pro Gln Ala His
450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
            485                 490                 495

Ala Gly Thr Thr Asp Ala Ala His Pro Gly Tyr Ser Arg Val Gly Ala
            500                 505                 510

Ala Gly Arg Phe Glu Gln Thr Lys Pro Ser Gln Leu Gln Ser Arg Glu
            515                 520                 525

Leu Ser Gly Ser Arg Cys Pro Glu Pro Cys Asp Cys Ala Pro Asp Gly
530                 535                 540

Ala Leu Arg Cys Pro Gly Pro Arg Ala Gly Leu Ala Arg Leu Ser Leu
545                 550                 555                 560

Thr Tyr Leu Pro Val Lys Val Ile Pro Ser Gln Ala Phe Arg Gly Leu
                565                 570                 575

Asn Glu Val Val Lys Ile Glu Ile Ser Gln Ser Asp Ser Leu Glu Arg
                580                 585                 590

Ile Glu Ala Asn Ala Phe Asp Asn Leu Leu Asn Leu Ser Glu Leu Leu
            595                 600                 605

Ile Gln Asn Thr Lys Asn Leu Leu Tyr Ile Glu Pro Gly Ala Phe Thr
610                 615                 620

Asn Leu Pro Arg Leu Lys Tyr Leu Ser Ile Cys Asn Thr Gly Ile Arg
625                 630                 635                 640

Thr Leu Pro Asp Val Thr Lys Ile Ser Ser Ser Glu Phe Asn Phe Ile
                645                 650                 655

Leu Glu Ile Cys Asp Asn Leu His Ile Thr Ser Ile Pro Val Asn Ala
            660                 665                 670

Phe Gln Gly Leu Cys Asn Glu Thr Leu Thr Leu Lys Leu Tyr Asn Asn
            675                 680                 685

Gly Phe Thr Ser Val Gln Gly Tyr Ala Phe Asn Gly Thr Lys Leu Asp
690                 695                 700

Ala Val Tyr Leu Asn Lys Asn Lys Tyr Leu Thr Val Ile Asp Lys Asp
705                 710                 715                 720

Ala Phe Gly Gly Val Tyr Ser Gly Pro Ser Leu Leu Asp Val Ser Gln
                725                 730                 735

Thr Ser Val Thr Ala Leu Pro Ser Lys Gly Leu Glu His Leu Lys Glu
            740                 745                 750

Leu Ile Ala Arg Asn Thr Trp Thr Leu Lys Lys Leu Pro Leu Ser Leu
            755                 760                 765

Ser Phe Leu His Leu Thr Arg Ala Asp Leu Ser Tyr Pro Ser His Cys
770                 775                 780

Cys Ala Phe Lys Asn Gln Lys Lys Ile Arg Gly Ile Leu Glu Ser Leu
785                 790                 795                 800

Met Cys Asn Glu Ser Ser Met Gln Ser Leu Arg Gln Arg Lys Ser Val
                805                 810                 815

Asn Ala Leu Asn Ser Pro Leu His Gln Glu Tyr Glu Glu Asn Leu Gly
            820                 825                 830

Asp Ser Ile Val Gly Tyr Lys Glu Lys Ser Lys Phe Gln Asp Thr His
            835                 840                 845

Asn Asn Ala His Tyr Tyr Val Phe Glu Glu Gln Glu Asp Glu Ile
850                 855                 860

Ile Gly Phe Gly Gln Glu Leu

<210> SEQ ID NO 7
<211> LENGTH: 1179
<212> TYPE: DNA
<213> ORGANISM: Homo sapiens

<400> SEQUENCE: 7

```
atgaggccgg cggacttgct gcagctgcag ctgctggtgc tggcagtgct gctgctgaag      60
ccttcacagc tgcagtcccg agagctgtca gggtcgcgct gccccgagcc ctgcgactgc     120
gcaccggatg gcgccctgcg ctgtcctggc cctcgagccg gcctcgccag actatctctc     180
acctatctcc ctgtcaaagt aattccatca caagctttca ggggacttaa tgaggtcgta     240
aaaattgaaa tctctcagag tgattccctg gaaaggatag aagctaatgc ctttgacaac     300
ctcctcaatt tgtctgaact actgatccag aacaccaaaa acctgctata cattgaacct     360
ggtgctttta caaacctccc tcggttaaaa tacctgagca tctgtaacac aggcatccga     420
acccttccag atgttacgaa gatctcctcc tctgaattta atttcattct ggaaatctgt     480
gataacttac acataaccct aatccctgtg aatgcttttc agggactatg caatgaaacc     540
ttgacactga agctgtacaa caacggcttt acttcagtcc aaggatatgc tttcaatggg     600
acaaagctgg atgctgttta cctaaacaag aataaatacc tgacagttat tgacaaagat     660
gcatttggag gagtatacag tggaccaagc ttgctggacg tgtctcaaac cagtgtcact     720
gcccttccat ccaaaggcct ggagcacctg aaggaactga tagcaagaaa cacctggact     780
cttaagaaac ttccactttc cttgagtttc cttcacctca cacgggctga cctttcttac     840
ccaagccact gctgtgcctt taagaatcag aagaaaatca aggaatcct tgagtccttg     900
atgtgtaatg agagcagtat gcagagcttg cgccagagaa atctgtgaa tgccttgaat     960
agccccctcc accaggaata tgaagagaat ctgggtgaca gcattgttgg gtacaaggaa    1020
aagtccaagt ccaggatac tcataacaac gctcattatt acgtcttctt tgaagaacaa    1080
gaggatgaga tcattggttt tggccaggag ctcgaaaaat cccatctaac cccaaagaag    1140
caaggccaaa tctcagaaga gtatatgcaa acggtttaa                            1179
```

<210> SEQ ID NO 8
<211> LENGTH: 392
<212> TYPE: PRT
<213> ORGANISM: Homo sapiens

<400> SEQUENCE: 8

```
Met Arg Pro Ala Asp Leu Leu Gln Leu Gln Leu Leu Val Leu Ala Val
1               5                   10                  15

Leu Leu Leu Lys Pro Ser Gln Leu Gln Ser Arg Glu Leu Ser Gly Ser
            20                  25                  30

Arg Cys Pro Glu Pro Cys Asp Cys Ala Pro Asp Gly Ala Leu Arg Cys
        35                  40                  45

Pro Gly Pro Arg Ala Gly Leu Ala Arg Leu Ser Leu Thr Tyr Leu Pro
    50                  55                  60

Val Lys Val Ile Pro Ser Gln Ala Phe Arg Gly Leu Asn Glu Val Val
65                  70                  75                  80

Lys Ile Glu Ile Ser Gln Ser Asp Ser Leu Glu Arg Ile Glu Ala Asn
                85                  90                  95

Ala Phe Asp Asn Leu Leu Asn Leu Ser Glu Leu Leu Ile Gln Asn Thr
            100                 105                 110
```

```
Lys Asn Leu Leu Tyr Ile Glu Pro Gly Ala Phe Thr Asn Leu Pro Arg
            115                 120                 125

Leu Lys Tyr Leu Ser Ile Cys Asn Thr Gly Ile Arg Thr Leu Pro Asp
        130                 135                 140

Val Thr Lys Ile Ser Ser Glu Phe Asn Phe Ile Leu Glu Ile Cys
145                 150                 155                 160

Asp Asn Leu His Ile Thr Ser Ile Pro Val Asn Ala Phe Gln Gly Leu
                165                 170                 175

Cys Asn Glu Thr Leu Thr Leu Lys Leu Tyr Asn Asn Gly Phe Thr Ser
            180                 185                 190

Val Gln Gly Tyr Ala Phe Asn Gly Thr Lys Leu Asp Ala Val Tyr Leu
        195                 200                 205

Asn Lys Asn Lys Tyr Leu Thr Val Ile Asp Lys Asp Ala Phe Gly Gly
210                 215                 220

Val Tyr Ser Gly Pro Ser Leu Leu Asp Val Ser Gln Thr Ser Val Thr
225                 230                 235                 240

Ala Leu Pro Ser Lys Gly Leu Glu His Leu Lys Glu Leu Ile Ala Arg
                245                 250                 255

Asn Thr Trp Thr Leu Lys Lys Leu Pro Leu Ser Leu Ser Phe Leu His
            260                 265                 270

Leu Thr Arg Ala Asp Leu Ser Tyr Pro Ser His Cys Cys Ala Phe Lys
        275                 280                 285

Asn Gln Lys Lys Ile Arg Gly Ile Leu Glu Ser Leu Met Cys Asn Glu
    290                 295                 300

Ser Ser Met Gln Ser Leu Arg Gln Arg Lys Ser Val Asn Ala Leu Asn
305                 310                 315                 320

Ser Pro Leu His Gln Glu Tyr Glu Glu Asn Leu Gly Asp Ser Ile Val
                325                 330                 335

Gly Tyr Lys Glu Lys Ser Lys Phe Gln Asp Thr His Asn Asn Ala His
            340                 345                 350

Tyr Tyr Val Phe Phe Glu Glu Gln Glu Asp Glu Ile Ile Gly Phe Gly
        355                 360                 365

Gln Glu Leu Glu Lys Ser His Leu Thr Pro Lys Lys Gln Gly Gln Ile
    370                 375                 380

Ser Glu Glu Tyr Met Gln Thr Val
385                 390
```

<210> SEQ ID NO 9
<211> LENGTH: 1323
<212> TYPE: DNA
<213> ORGANISM: Homo sapiens

<400> SEQUENCE: 9

| | |
|---|---|
| atgggagtca aagttctgtt tgccctgatc tgcatcgctg tggccgaggc caagcccacc | 60 |
| gagaacaacg aagacttcaa catcgtggcc gtggccagca acttcgcgac cacggatctc | 120 |
| gatgctgacc gcgggaagtt gcccggcaag aagctgccgc tggaggtgct caaagagatg | 180 |
| gaagccaatg cccggaaagc tggctgcacc aggggctgtc tgatctgcct gtcccacatc | 240 |
| aagtgcacgc ccaagatgaa gaagttcatc ccaggacgct gccacaccta cgaaggcgac | 300 |
| aaagagtccg cacagggcgg cataggcgag gcgatcgtcg acattcctga gattcctggg | 360 |
| ttcaaggact ggagcccat ggagcagttc atcgcacagg tcgatctgtg tgtggactgc | 420 |
| acaactggct gcctcaaagg gcttgccaac gtgcagtgtt ctgacctgct caagaagtgg | 480 |
| ctgccgcaac gctgtgcgac ctttgccagc aagatccagg ccaggtgga caagatcaag | 540 |

-continued

```
ggggccggtg gtgacagcat cggaatgggg tgttcgtctc caccctgcga gtgccatcag      600
gaggaggact tcagagtcac ctgcaaggat attcaacgca tccccagctt accgccagt       660 acgcagactc tgaagcttat tgagactcac ctgagaacta ttccaagtca tgcattttct      720
aatctgccca atatttccag aatctacgta tctatagatg tgactctgca gcagctggaa      780
tcacactcct tctacaattt gagtaaagtg actcacatag aaattcggaa taccaggaac      840
ttaacttaca tagaccctga tgccctcaaa gagctccccc tcctaaagtt ccttggcatt      900
ttcaacactg gacttaaaat gttccctgac ctgaccaaag tttattccac tgatatattc      960
tttatacttg aaattacaga caacccttac atgacgtcaa tccctgtgaa tgcttttcag     1020
ggactatgca atgaaacctt gacactgaag ctgtacaaca atggctttac ttcagtccaa     1080
ggatatgctt tcaatgggac aaagctggat gctgtttacc taaacaagaa taaatacctg     1140
acagttattg acaaagatgc atttggagga gtatacagtg accaagcttg ctggacgtg      1200 tctcaaaccg gtgtcactgc ccttccatcc aaaggcctgg agcacctgaa ggaactgata     1260
gcaagaaaca cctggactct aagaaaaaca ctgccctcca acatcacca tcaccatcac      1320 taa                                                                   1323

<210> SEQ ID NO 10
<211> LENGTH: 440
<212> TYPE: PRT
<213> ORGANISM: Homo sapiens

<400> SEQUENCE: 10

Met Gly Val Lys Val Leu Phe Ala Leu Ile Cys Ile Ala Val Ala Glu
  1               5                  10                  15

Ala Lys Pro Thr Glu Asn Asn Glu Asp Phe Asn Ile Val Ala Val Ala
                 20                  25                  30

Ser Asn Phe Ala Thr Thr Asp Leu Asp Ala Asp Arg Gly Lys Leu Pro
             35                  40                  45

Gly Lys Lys Leu Pro Leu Glu Val Leu Lys Glu Met Glu Ala Asn Ala
         50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                 85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
            115                 120                 125

Gln Phe Ile Ala Gln Val Asp Leu Cys Val Asp Cys Thr Thr Gly Cys
        130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp Ser Ile Gly Met Gly Cys Ser
            180                 185                 190

Ser Pro Pro Cys Glu Cys His Gln Glu Glu Asp Phe Arg Val Thr Cys
        195                 200                 205

Lys Asp Ile Gln Arg Ile Pro Ser Leu Pro Ser Thr Gln Thr Leu
    210                 215                 220
```

Lys Leu Ile Glu Thr His Leu Arg Thr Ile Pro Ser His Ala Phe Ser
225                 230                 235                 240

Asn Leu Pro Asn Ile Ser Arg Ile Tyr Val Ser Ile Asp Val Thr Leu
            245                 250                 255

Gln Gln Leu Glu Ser His Ser Phe Tyr Asn Leu Ser Lys Val Thr His
        260                 265                 270

Ile Glu Ile Arg Asn Thr Arg Asn Leu Thr Tyr Ile Asp Pro Asp Ala
    275                 280                 285

Leu Lys Glu Leu Pro Leu Leu Lys Phe Leu Gly Ile Phe Asn Thr Gly
290                 295                 300

Leu Lys Met Phe Pro Asp Leu Thr Lys Val Tyr Ser Thr Asp Ile Phe
305                 310                 315                 320

Phe Ile Leu Glu Ile Thr Asp Asn Pro Tyr Met Thr Ser Ile Pro Val
                325                 330                 335

Asn Ala Phe Gln Gly Leu Cys Asn Glu Thr Leu Thr Leu Lys Leu Tyr
            340                 345                 350

Asn Asn Gly Phe Thr Ser Val Gln Gly Tyr Ala Phe Asn Gly Thr Lys
        355                 360                 365

Leu Asp Ala Val Tyr Leu Asn Lys Asn Lys Tyr Leu Thr Val Ile Asp
    370                 375                 380

Lys Asp Ala Phe Gly Gly Val Tyr Ser Gly Pro Ser Leu Leu Asp Val
385                 390                 395                 400

Ser Gln Thr Ser Val Thr Ala Leu Pro Ser Lys Gly Leu Glu His Leu
                405                 410                 415

Lys Glu Leu Ile Ala Arg Asn Thr Trp Thr Leu Lys Lys Thr Leu Pro
            420                 425                 430

Ser Lys His His His His His His
        435                 440

<210> SEQ ID NO 11
<211> LENGTH: 30
<212> TYPE: DNA
<213> ORGANISM: Homo sapiens

<400> SEQUENCE: 11
gtcatgcatc agctgctggt gctggcagtg                                     30

<210> SEQ ID NO 12
<211> LENGTH: 30
<212> TYPE: DNA
<213> ORGANISM: Homo sapiens

<400> SEQUENCE: 12
gtcgacgtcg ttatgtgtaa gttatcacag                                     30

<210> SEQ ID NO 13
<211> LENGTH: 33
<212> TYPE: DNA
<213> ORGANISM: Homo sapiens

<400> SEQUENCE: 13
gtccttaaga aaacactgcc ctccaaagaa aaa                                  33

<210> SEQ ID NO 14
<211> LENGTH: 30
<212> TYPE: DNA
<213> ORGANISM: Homo sapiens

<400> SEQUENCE: 14

```
atcgagctct tcattctcct caaagatggc                                        30

<210> SEQ ID NO 15
<211> LENGTH: 27
<212> TYPE: DNA
<213> ORGANISM: Homo sapiens

<400> SEQUENCE: 15
tacgatatcg gaatggggtg ttcgtct                                           27

<210> SEQ ID NO 16
<211> LENGTH: 30
<212> TYPE: DNA
<213> ORGANISM: Homo sapiens

<400> SEQUENCE: 16
tatggatcct tatttggagg gcagtgtttt                                        30

<210> SEQ ID NO 17
<211> LENGTH: 36
<212> TYPE: DNA
<213> ORGANISM: Homo sapiens

<400> SEQUENCE: 17
tacgatatca tgctgctgct gctgctgctg ctgggc                                 36

<210> SEQ ID NO 18
<211> LENGTH: 27
<212> TYPE: DNA
<213> ORGANISM: Homo sapiens

<400> SEQUENCE: 18
tacagcgctt gtctgctcga agcggcc                                           27
```